United States Patent
Yamaguchi et al.

(10) Patent No.: US 11,427,779 B2
(45) Date of Patent: *Aug. 30, 2022

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Yuta Yamaguchi, Kawasaki (JP); Daisuke Yagyu, Ichihara (JP); Naoya Fukumoto, Ichihara (JP); Shoko Uetake, Ichihara (JP); Tsuyoshi Kato, Ichihara (JP); Hiroyuki Tomita, Ichihara (JP); Ryuuta Miyasaka, Ichihara (JP); Katsumi Murofushi, Ichihara (JP)

(73) Assignee: SHOWA DENKO K.K., Tokyo (JP)

( * ) Notice: Subject to any disclaimer, the term of this patent is extended or adjusted under 35 U.S.C. 154(b) by 270 days.

This patent is subject to a terminal disclaimer.

(21) Appl. No.: 16/480,483

(22) PCT Filed: Jan. 5, 2018

(86) PCT No.: PCT/JP2018/000071
§ 371 (c)(1),
(2) Date: Jul. 24, 2019

(87) PCT Pub. No.: WO2018/139174
PCT Pub. Date: Aug. 2, 2018

(65) Prior Publication Data
US 2019/0382676 A1    Dec. 19, 2019

(30) Foreign Application Priority Data
Jan. 26, 2017  (JP) .............................. JP2017-012344

(51) Int. Cl.
*C10M 107/46* (2006.01)
*G11B 5/72* (2006.01)
(Continued)

(52) U.S. Cl.
CPC ......... *C10M 107/46* (2013.01); *C07D 213/68* (2013.01); *C07D 231/12* (2013.01);
(Continued)

(58) Field of Classification Search
CPC .... G11B 5/725; G11B 5/7257; C10M 107/46; C10M 107/44; C10M 2221/0405;
(Continued)

(56) References Cited

U.S. PATENT DOCUMENTS 6,323,163 B1   11/2001   Sasaki et al.
11,011,200 B2 *   5/2021   Uetake .................. G11B 5/725
(Continued)

FOREIGN PATENT DOCUMENTS

JP         11-60720 A    3/1999
JP      2010-143855 A    7/2010
(Continued)

OTHER PUBLICATIONS

International Search Report for PCT/JP2018/000071 dated Mar. 6, 2018 [PCT/ISA/210].
(Continued)

*Primary Examiner* — Holly Rickman
(74) *Attorney, Agent, or Firm* — Sughrue Mion, PLLC

(57) ABSTRACT

A fluorine-containing ether compound represented by Formula (1) is provided.

$$R^1-R^2-CH_2-R^3-CH_2-R^4-R^5 \quad (1)$$

(In Formula (1), $R^1$ and $R^5$ each represents a group having a heterocyclic ring and may be the same as or different from each other, $R^2$ and $R^4$ each represents a divalent linking group having a polar group and play be the same as or different from each other, and $R^3$ represents a perfluoropolyether chain.)

11 Claims, 1 Drawing Sheet

(51) Int. Cl.

| | |
|---|---|
| *G11B 5/725* | (2006.01) |
| *C10N 40/18* | (2006.01) |
| *C07D 213/68* | (2006.01) |
| *C07D 231/12* | (2006.01) |
| *C07D 277/24* | (2006.01) |
| *C07D 333/16* | (2006.01) |
| *C07D 409/12* | (2006.01) |
| *C08G 65/333* | (2006.01) |
| *C08G 65/334* | (2006.01) |
| *C10M 107/44* | (2006.01) |

(52) U.S. Cl.
CPC ......... *C07D 277/24* (2013.01); *C07D 333/16* (2013.01); *C07D 409/12* (2013.01); *C08G 65/3344* (2013.01); *C08G 65/3348* (2013.01); *C08G 65/33396* (2013.01); *C10M 107/44* (2013.01); *G11B 5/7257* (2020.08); *G11B 5/7266* (2020.08); *G11B 5/7268* (2020.08); *C10M 2217/065* (2013.01); *C10M 2221/0405* (2013.01); *C10N 2040/18* (2013.01)

(58) Field of Classification Search
CPC ........... C10M 2217/065; C07D 409/12; C07D 213/68; C07D 213/12; C07D 277/24; C07D 333/16; C08G 65/33396; C08G 65/3344; C08G 65/3348; C10N 2040/18
See application file for complete search history.

(56) References Cited

U.S. PATENT DOCUMENTS

| | | | |
|---|---|---|---|
| 2006/0111251 A1 | 5/2006 | Tonelli et al. | |
| 2010/0261039 A1* | 10/2010 | Itoh | G11B 5/8408 |
| | | | 428/800 |
| 2012/0008228 A1* | 1/2012 | Mabuchi | G11B 5/725 |
| | | | 360/55 |
| 2013/0209837 A1 | 8/2013 | Sagata et al. | |
| 2015/0371672 A1 | 12/2015 | Sagata | |
| 2019/0185621 A1 | 6/2019 | Naitou et al. | |

FOREIGN PATENT DOCUMENTS

| | | |
|---|---|---|
| JP | 2012-009090 A | 1/2012 |
| JP | 2012-33253 A | 2/2012 |
| JP | 2013-163667 A | 8/2013 |
| JP | 2013-181014 A | 9/2013 |
| JP | 2013-181140 A | 9/2013 |
| JP | 5465454 B2 | 1/2014 |
| JP | 5613916 B2 | 10/2014 |
| JP | 2018-035348 A | 3/2018 |
| WO | 98/17617 A1 | 4/1998 |
| WO | 2009/123043 A1 | 10/2009 |
| WO | 2011/099131 A1 | 8/2011 |
| WO | 2015/087615 A1 | 6/2015 |

OTHER PUBLICATIONS

Notice of Reasons for Rejection dated Dec. 24, 2019, from the Japanese Patent Office in Application No. 2016-133653.
Requirement for Election/Restriction dated Jun. 10, 2019 issued in U.S. Appl. No. 15/640,729.
Non-Final Office Action dated Oct. 29, 2019 issued in U.S. Appl. No. 15/640,729.
Non-Final Office Action dated May 13, 2020 issued in U.S. Appl. No. 15/640,729.
Final Office Action dated Nov. 12, 2020 issued in U.S. Appl. No. 15/640,729.
Notice of Allowance dated Feb. 8, 2021 issued in U.S. Appl. No. 15/640,729.
Supplemental Notice of Allowance dated Mar. 4, 2021 issued in U.S. Appl. No. 15/640,729.

* cited by examiner

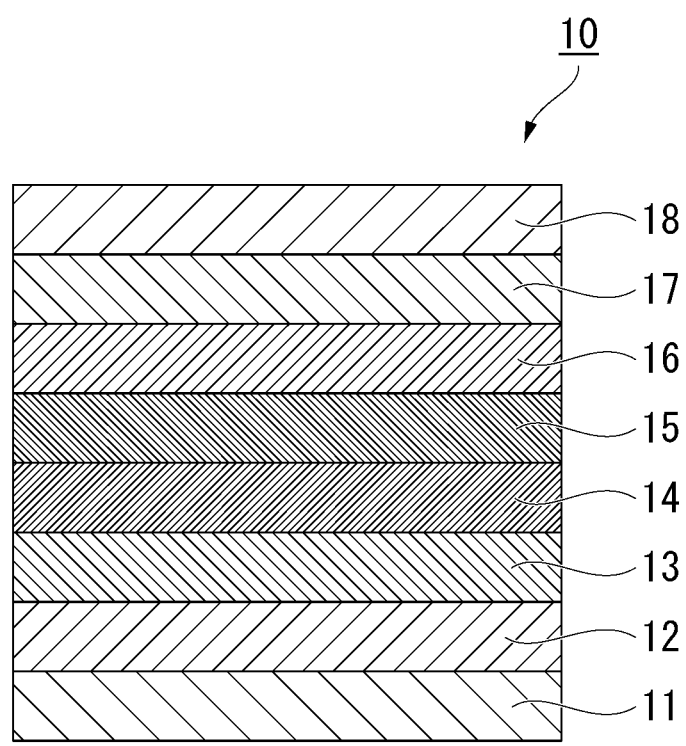

FLUORINE-CONTAINING ETHER COMPOUND, LUBRICANT FOR MAGNETIC RECORDING MEDIUM, AND MAGNETIC RECORDING MEDIUM

This application is a National Stage of International Application No. PCT/JP2018/000071, filed on Jan. 5, 2018, which claims priority from Japanese Patent Application No. 2017-012344, filed on Jan. 26, 2017, the content of which is incorporated herein by reference.

TECHNICAL FIELD

The present invention relates to a fluorine-containing ether compound suitable for a lubricant application of a magnetic recording medium.

BACKGROUND ART

With an increase in capacity of information processing of recent years, various information-recording technologies have been developed. In particular, development of a magnetic recording medium suitable for high recording density is in progress.

A magnetic recording medium generally includes a protective layer and a lubricating layer on a magnetic recording layer formed on a substrate, in order to ensure durability and reliability of the magnetic recording medium. In particular, the lubricating layer used for an outermost surface is required to have various characteristics such as long-term stability, chemical resistance (preventing contamination with siloxane and the like), and wear resistance.

A perfluoropolyether lubricant including an aromatic group at an end of a molecule has often been used as a lubricant for a magnetic recording medium. For example, Patent documents 1 and 2 disclose a lubricating layer including a perfluoroalkylpolyether compound having an aromatic group and a hydroxyl group at the end of the molecule. Patent document 1 describes a magnetic disk that has excellent load unload (LUL) durability and alumina resistance (preventing a lubricant from being decomposed by alumina). In addition, Patent document 2 discloses a perfluoropolyether compound having excellent low scattering property. Further, Patent document 3 discloses a magnetic recording medium in which a lubricating layer includes a perfluoropolyether lubricant including a compound having a heterocyclic group at an end of a molecule, and which has excellent corrosion resistance.

CITATION LIST

Patent Documents

Patent document 1: Japanese Patent No. 5465454
Patent document 2: Japanese Patent No. 5613916
Patent document 3: Japanese Unexamined Patent Application, First Publication No. 2012-33253

SUMMARY OF INVENTION

Technical Problem

In recent years, with the rapid improvement in information recording density of a magnetic disk, it is required to reduce magnetic spacing between a magnetic head and a recording layer of the magnetic disk. Therefore, the lubricating layer present between the magnetic head and the recording layer of the magnetic disk is required to be further thinned. The lubricant used for the lubricating layer disposed on an outermost surface of the magnetic disk has a significant influence on the reliability of the magnetic disk. Therefore, it is necessary to make the lubricating layer thinner while securing the reliability such as wear resistance, which is indispensable for the magnetic disk.

In addition, according to diversification of applications of the magnetic disk, remarkably high environmental resistance is required for the magnetic disk. Therefore, it is required to further improve the wear resistance and chemical resistance of the lubricating layer, which has a significant influence on the reliability of the magnetic disk.

However, in general, when a thickness of the lubricating layer is reduced, coverage tends to deteriorate and the chemical resistance and the wear resistance tend to deteriorate.

The present invention was made in view of the above circumstances, and an object thereof is to provide a fluorine-containing ether compound, which can be suitably used as a material of a lubricant for a magnetic recording medium, wherein the material can form a lubricating layer having excellent chemical resistance and wear resistance, even when the thickness is reduced.

In addition, another object of the present invention is to provide a lubricant for a magnetic recording medium, including the fluorine-containing ether compound of the present invention.

In addition, still another object of the present invention is to provide a magnetic recording medium which includes a lubricating layer including the fluorine-containing ether compound of the present invention.

Solution to Problem

The present inventors have intensively studied to achieve the above objects.

As a result, in order to achieve the above objects, it was found that a fluorine-containing ether compound in which a group having a heterocyclic ring is bonded to each of both ends of a perfluoropolyether chain via a divalent linking group having a polar group may be used for a lubricant, and the present invention was conceived.

That is, the present invention relates to the following aspects.

[1] A fluorine-containing ether compound represented by Formula (1).

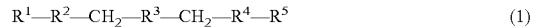

$$R^1-R^2-CH_2-R^3-CH_2-R^4-R^5 \qquad (1)$$

(in Formula (1), $R^1$ and $R^5$ each represents a group having a heterocyclic, ring and may be the same as or different from each other, $R^2$ and $R^4$ each represents a divalent linking group having a polar group and may be the same as or different from each other, and $R^3$ represents a perfluoropolyether chain)

[2] The fluorine-containing ether compound according to [1], in which the heterocyclic ring includes one or more heteroatoms and the heteroatom is a nitrogen atom and/or a sulfur atom.

[3] The fluorine-containing ether compound according to [1], in which the heterocyclic ring is at least one selected from the group consisting of a pyrazole ring, a thiophene ring, a thiazole ring, and a pyridine ring.

[4] The fluorine-containing ether compound according to any one of [1] to [3], in which the polar group is a hydroxyl group.

[5] The fluorine-containing ether compound according to any one of [1] to [4], in which $R^2$ and $R^4$ in Formula (1) are each represented by Formula (2-1) or (2-2).

$$—(O—CH_2CH(OH)CH_2)_a—O— \qquad (2\text{-}1)$$

(in Formula (2-1), a represents an integer selected from 1 to 3)

$$—(O—CH_2CH(CH_2OH)CH_2)_b—O— \qquad (2\text{-}2)$$

(in Formula (2-2), b represents an integer selected from 1 to 3)

[6] The fluorine-containing ether compound according to any one of [1] to [5], in which $R^3$ in Formula (1) is represented by any of Formulas (3) to (5).

$$—CF_2—(OCF_2CF_2)_c—(OCF_2)_d—OCF_2— \qquad (3)$$

(in Formula (3), c and d each represents 0 to 20, where c or d is 0.1 or more)

$$—CF(CF_3)—(OCF(CF_3)CF_2)_e—OCF(CF_3)— \qquad (4)$$

(in Formula (4), e represents 0.1 to 20)

$$—CF_2CF_2—(OCF_2CF_2CF_2)_f—OCF_2CF_2— \qquad (5)$$

(in Formula (5), f represents 0.1 to 20)

[7] The fluorine-containing ether compound according to any one of [1] to [6], in which a number-average molecular weight is within a range of 500 to 10000.

[8] A lubricant for a magnetic recording medium, including the fluorine-containing ether compound according to any one of [1] to [7].

[9] A magnetic recording medium including: a substrate; and at least a magnetic layer, a protective layer, and a lubricating layer sequentially provided on the substrate, in which the lubricating layer includes the fluorine-containing ether compound according to any one of [1] to [7].

[10] The magnetic recording medium according to [9], in which an average film thickness of the lubricating layer is 0.5 nm to 2 nm.

Advantageous Effects of Invention

The fluorine-containing ether compound of the present invention is a compound represented by Formula (1), and is suitable as a material for a lubricant for a magnetic recording medium.

Since the lubricant for a magnetic recording medium of the present invention includes the fluorine-containing ether compound of the present invention, it is possible to form a lubricating layer having excellent chemical resistance and wear resistance even when the thickness thereof is reduced.

Since the magnetic recording medium of the present invention includes a lubricating layer having excellent chemical resistance and wear resistance, it has excellent durability.

BRIEF DESCRIPTION OF DRAWINGS

FIG. 1 is a schematic sectional view showing an embodiment of a magnetic recording medium according to the present invention.

BEST MODE FOR CARRYING OUT THE INVENTION

Hereinafter, preferred examples of a fluorine-containing ether compound, a lubricant for a magnetic recording medium, and a magnetic recording medium of the present invention are described in detail. The present invention is not limited to only the embodiments shown below.

[Fluorine-Containing Compound]

The fluorine-containing ether compound of the present embodiment is represented by Formula (1) below.

$$R^1—R^2—CH_2R^3—CH_2—R^4—R^5 \qquad (1)$$

(In Formula (1), $R^1$ and $R^5$ each represents a group having a heterocyclic ring and may be the same as or different from each other, $R^2$ and $R^4$ each represents a divalent linking group having a polar group and may be the same as or different from each other, and $R^3$ represents a perfluoropolyether chain.)

In the fluorine-containing ether compound represented by Formula (1) of the present embodiment, $R^1$ and $R^5$ each represents group having a heterocyclic ring. In the fluorine-containing ether compound of the present embodiment, the heterocyclic ring in $R^1$ and the polar group in $R^2$, and the heterocyclic ring in $R^5$ and the polar group in $R^4$ in the lubricating layer exhibit favorable interaction with the protective layer respectively. The group having a heterocyclic ring can be appropriately selected according to performance or the like required for the lubricant including the fluorine-containing ether compound.

Each of $R^1$ and $R^5$ is preferably a group having a heterocyclic ring represented by any of Formulas (6) to (9). Among these, a group having a heterocyclic ring represented by any of Formulas (7) to (9) is particularly preferable. In a case where $R^1$ is a group having a heterocyclic ring represented by any of Formulas (7) to (9), a distance between the heterocyclic ring in $R^1$ and the polar group in $R^2$ is appropriate, and the affinity between the lubricating layer including the fluorine-containing ether compound and the protective layer is further favorable. Similarly, in a case where $R^5$ is a group having a heterocyclic ring represented by any of Formulas (7) to (9), a distance between the heterocyclic ring in $R^5$ and the polar group in $R^4$ is appropriate, and the affinity between the lubricating layer including the fluorine-containing ether compound and the protective layer is further favorable.

$$Z— \qquad (6)$$

(In Formula (6), Z represents a heterocyclic ring which may have a substituent.)

$$Z—O—(CH_2)_g— \qquad (7)$$

(In Formula (7), Z represents a heterocyclic ring which may have a substituent, and g represents an integer selected from 1 to 3.)

$$Z—(CH_2)_h— \qquad (8)$$

(In Formula (8), Z represents a heterocyclic ring which may have a substituent, and h represents an integer selected from 1 to 3.)

$$Z—(CH_2)_i—O—(CH_2)_j— \qquad (9)$$

(In Formula (9), Z is a heterocyclic ring which may have a substituent. i and j each represents an integer selected from 1 to 3.)

Here, the integer of 1 to 3 means that any number of 1, 2, and 3 may be used.

In Formulas (7) to (9), when g, h, i, and j each represents an integer of 1 or more, a distance between the heterocyclic ring in $R^1$ and the polar group in $R^2$ and/or a distance between the heterocyclic ring included in $R^5$ and the polar group included in $R^4$ is sufficiently secured. Therefore, the interaction between the heterocyclic ring included in $R^1$ and the polar group included in $R^2$ and/or the interaction between the heterocyclic ring included in $R^5$ and the polar group included in $R^4$ is sufficiently suppressed. As a result, the affinity between the lubricating layer including the fluorine-containing ether compound and the protective layer is further favorable. In addition, in Formulas (7) to (9), when g, h, i, and j represent an integer of 3 or less, a distance between the heterocyclic ring in $R^1$ and the polar group in $R^2$ and/or a distance between the heterocyclic ring included in $R^5$ and the polar group included in $R^4$ is not too long. Therefore, the degree of freedom of the heterocyclic ring in the lubricating layer including the fluorine-containing ether compound is not too large, and the distance between the heterocyclic ring included in $R^1$ and the polar group included in $R^2$, and/or the distance between the heterocyclic ring included in $R^5$ and the polar group included in $R^4$ is appropriate. In the lubricating layer including the heterocyclic rings and the polar groups, a favorable interaction with the protective layer is exhibited.

Preferred examples of the heteroatom in the heterocyclic ring include a nitrogen atom, a sulfur atom, an oxygen atom, a phosphorus atom, a boron atom, and a selenium atom. The number of heteroatoms in the heterocyclic ring is not limited and is, for example, 1, 2, 3, or 4. The number of the kind of heteroatom included in the heterocyclic ring is not limited and is, for example, 1, 2, 3, or 4. Among the examples of these heteroatoms, the nitrogen atom, the sulfur atom, and the oxygen atom are preferable, and the nitrogen atom and/or the sulfur atom is particularly preferable. The heterocyclic ring in which the heteroatom is the nitrogen atom and/or the sulfur atom has a large interaction with the protective layer, in particular, the protective layer formed of a carbon-based material. Therefore, when the heteroatom of the heterocyclic ring is the nitrogen atom and/or the sulfur atom, the lubricating layer including the fluorine-containing ether compound achieves further enhanced adhesion protective layer.

As described above, the number of heteroatoms included as a ring member atom of the heterocyclic ring is not particularly limited., but a heterocyclic ring including one or two heteroatoms is preferable from the viewpoint of the affinity to the protective layer.

The number of ring member atoms of the heterocyclic ring is not particularly limited, and is preferably 3 to 14 and particularly preferably 5 to 10. The heterocyclic ring may be a polycyclic ring or a single ring.

Specific examples of the heterocyclic ring can include rings such as pyrrole, imidazole, pyrazole, triazole, tetrazole, pyridine, pyridazine, pyrimidine, pyrazine, triazine, franc, oxazole, isoxazole, thiophene, thiazole, thiadiazole, piperidine, piperazine, morpholine, tetrahydrofuran, lactam, lactone, benzofuran, isobenzofuran, indole, isoindole, benzothiophene, purine, benzoxazole, benzothiazole, quinoline, isoquinoline, hydroquinoline, acridine, quinazoline, cinnoline, benzimidazole, benzotriazole, coumarin, and pteridine, but are not limited thereto. Among these, rings of pyrazole, thiophene, thiazole, and pyridine are particularly preferable, since these are capable of obtaining a fluorine-containing ether compound having favorable affinity to the protective layer.

The heterocyclic ring in the group having a heterocyclic ring may be substituted with a substituent or not be substituted. In a case where the heterocyclic ring has a substituent, the substituent is not particularly limited, and examples thereof include an alkyl group (for example, an alkyl group having 1 to 6 carbon atoms), a nitro group, a carboxyl group, a sulfo group, an amino group, a mercapto group, a hydroxyl group, and an aryl group (for example, a phenyl group).

$R^2$ and $R^4$ in Formula (1) each represents a divalent linking group having a polar group. Since $R^2$ and $R^4$ in Formula (1) each have a polar group, in a case where the lubricating layer is formed on the protective layer using a lubricant including the fluorine-containing ether compound of the present embodiment, favorable interaction occurs between the lubricating layer and the protective layer. The divalent linking group having a polar group can be appropriately selected according to performance or the like required for the lubricant including the fluorine-containing ether compound.

Examples of the polar group included in the divalent linking group having a polar group include a hydroxyl group (—OH), an amino group (—CO—), a carboxyl group (—COOH), an aldehyde group (—COH), a carbonyl group (—CO—), and a sulfonic acid group (—SO$_3$H). Among these, it is particularly preferable that the polar group be the hydroxyl group. The hydroxyl group has a large interaction with the protective layer, in particular, the protective layer formed of a carbon-based material. Therefore, when the polar group is the hydroxyl group, the lubricating layer including the fluorine-containing ether compound achieves further enhanced adhesion to the protective layer.

Each of $R^2$ and $R^4$ in Formula (1) is preferably represented by Formula (2-1) or (2-2).

—(O—CH$_2$CH(OH)CH$_2$)$_a$—O— $\quad$ (2-1)

(In Formula (2-1), a represents an integer selected from 1 to 3)

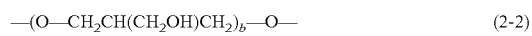

—(O—CH$_2$CH(CH$_2$OH)CH$_2$)$_b$—O— $\quad$ (2-2)

(In Formula (2-2), b represents an integer selected from 1 to 3)

When a in Formula (2-1) and b in Formula (2-2) each represents 1 or more, the interaction between the polar group included in $R^2$ and $R^4$ and the protective layer is further strengthened. As a result, a fluorine-containing ether compound capable of obtaining a lubricating layer having higher adhesion to the protective layer is obtained. In addition, when a and b each represents 3 or less, it is possible to prevent pickup from occurring, wherein the pickup is adhesion to a magnetic head as a foreign substance (smear) and is caused when the polarity of the fluorine-containing ether compound is too high.

In the fluorine-containing ether compound represented by Formula (1) of the present embodiment, each of $R^2$ and $R^4$ is preferably represented by Formula (2-1) or (2-2). In this case, a carbon atom and an oxygen atom bonded to each other in a chain shape (at least —O—CH$_2$—) are disposed between the heterocyclic ring included in $R^1$ or $R^5$ and a carbon atom to which the polar group in $R^2$ or $R^4$ is bonded. Therefore, the interaction between the heterocyclic ring and the polar group is weakened, for example, compared to a case where the heterocyclic ring included in $R^1$ or $R^5$ and the polar group included in $R^2$ or $R^4$ are bonded to the same carbon (heterocyclic ring-C(polar group)-). On the other hand, the interaction of the heterocyclic ring and the polar group and a functional group present in large numbers on the surface of the protective layer is relatively strengthened, compared to the case where the heterocyclic ring and the polar group are bonded to the same carbon. As a result, in a case where the lubricating layer is formed on the protective layer using the lubricant including the fluorine-containing ether compound, the affinity between the lubricating layer and the protective layer increases.

Therefore, in a case where each of $R^2$ and $R^4$ is represented by Formula (2-1) or (2-2), the lubricating layer formed using the lubricant including the fluorine-containing ether compound achieves further excellent chemical resistance and wear resistance. From the viewpoint of affinity between the lubricating layer and the protective layer, it is desirable that a total number of the carbon atom and the oxygen atom, which are bonded to each other in a chain shape and are present between the atom forming the heterocyclic ring included in $R^1$ or $R^5$ and the carbon to which the polar group included in $R^2$ or $R^4$ is bonded, be 2 to 4.

$R^3$ in Formula (1) represents a perfluoropolyether chain (hereinafter abbreviated as "PFPE chain" in some cases). In the lubricating layer including the fluorine-containing ether compound of the present embodiment, the PFPE chain covers the surface of the protective layer and reduces a frictional force between the magnetic head and the protective layer. The PFPE chain can be appropriately selected according to performance or the like required for the lubricant including the fluorine-containing ether compound.

Examples of the PFPE chain include a chain including a perfluoromethylene oxide polymer, a perfluoroethylene oxide polymer, a perfluoro-n-propylene oxide polymer, a perfluoroisopropylene oxide polymer, and a copolymer of these polymers.

Specifically, $R^3$ in Formula (1) is preferably one represented by any of Formulas (3) to (5). In a case where $R^3$ is one represented by any of Formulas (3) to (5), a fluorine-containing ether compound capable of obtaining a lubricating layer having favorable lubricity is obtained.

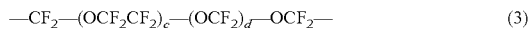

(In Formula (3), c and d each represents 0 to 20, where c or d is 0.1 or more)

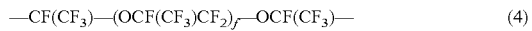

(In Formula (4), e represents 0,1 to 20.)

(In Formula (5), f represents 0.1 to 20.)

When e and f in Formulas (4) and (5) each represents 0.1 to 20 (or c and d in Formula (3) each represents 0 to 20, and c or d represents 0.1 or more), a fluorine-containing ether compound capable of obtaining a lubricating layer having more favorable lubricity is obtained. However, when c, d, e, and f exceed 20, viscosity of the fluorine-containing ether compound increases, and a lubricant including the compound may be difficult to be applied, in some cases. Therefore, c, d, e, and f are preferably 20 or less. The reason why c, d, e, and f, which are repetition numbers in the formula, may be numbers after the decimal point such as 0.1 is that it is a value indicating an average value. c, d, e, and f can be used without problems as long as these are in the range, but is more preferably 0.1 to 15, still more preferably 1 to 10, and particularly preferably 2 to 8. If c, d, e, and f are in the range of 0.1 to 20, preferable numerical values may be selected according to a required characteristic. For example, according to the required characteristic, c, d, e, and f are also preferably 0.1 to 3, 3 to 8, 8 to 13, and 13 to 20.

In the fluorine-containing ether compound represented by Formula (1), $R^1$ and $R^5$ may be the same as or different from each other. When $R^1$ and $R^5$ are the same as each other, easy production possible, which is preferable.

In addition, in the fluorine-containing ether compound represented by Formula (1), $R^2$ and $R^4$ may be the same as or different from each other. When $R^2$ and $R^4$ are the same as each other, easy production is possible, which is preferable.

Therefore, in the fluorine-containing ether compound represented by Formula (1) when $R^1$ and $R^5$ are the same as each other and $R^2$ and $R^4$ are the same as each other, easier production is possible, which is preferable.

Specifically, it is preferable that the fluorine-containing ether compound represented by Formula (1) be any of compounds represented by Formulas (A) to (F) and (I) to (L). In the compounds represented by Formulas (A) to (F) and (I) to (L), $R^1$ and $R^5$ each represents a group having a heterocyclic ring represented by Formula (6) or (8), each of $R^2$ and $R^4$ is represented by Formula (2-1), and $R^3$ is represented by Formula (3) or (5). Since the repetition number in the formula, such as q and r in Formula (A), is a value showing an average value, the number is not necessarily an integer.

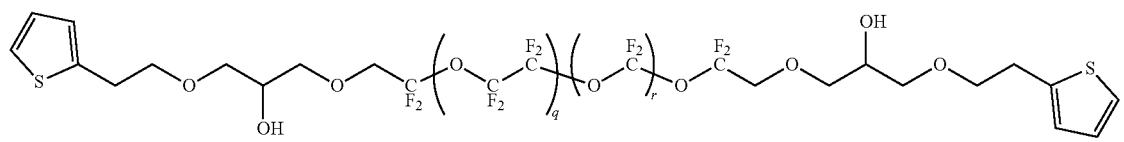

(In Formula (A), q and r each represents 0.1 to 20.)

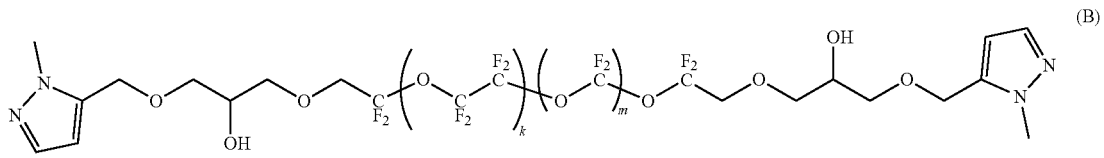

(In Formula (B), k and in each represents 0.1 to 20.)
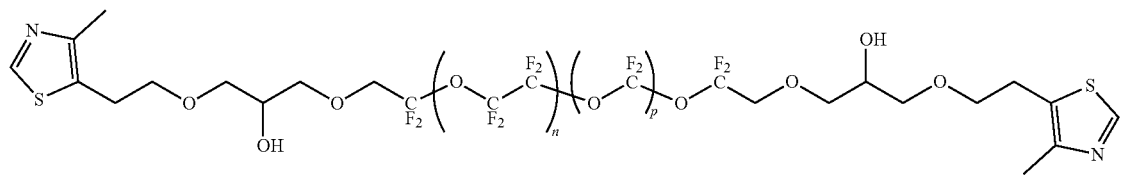
(C)
(In Formula (C), n and p each represents 0.1 to 20.)
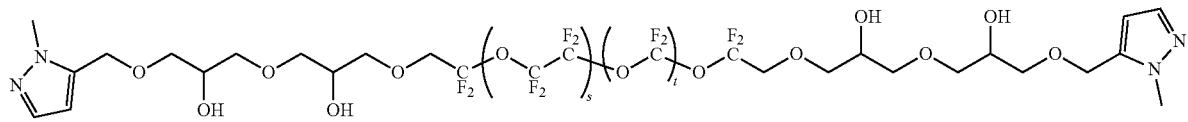
(D)
(In Formula (D), s and t each represents 0.1 to 20.)
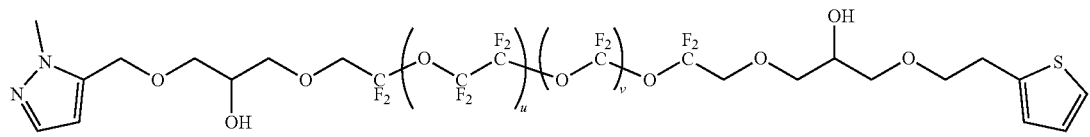
(E)
(In Formula (E), u and v each represents 0.1 to 20.)
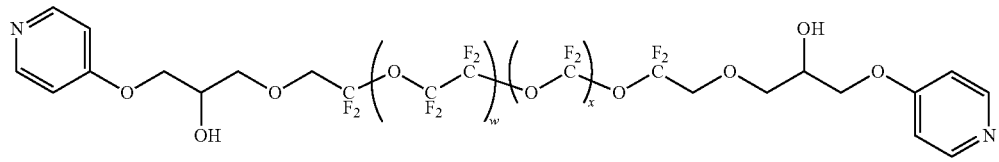
(F)
(In Formula (F), w and x each represents 0.1 to 20.)
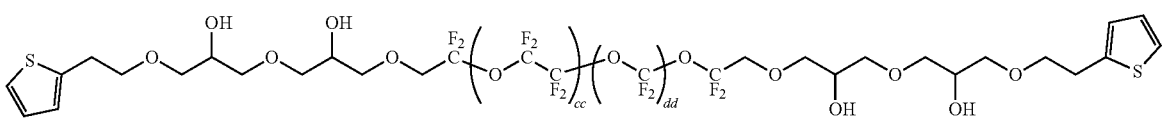
(I)
(In Formula (1), cc and dd each represents 0.1 to 20.)
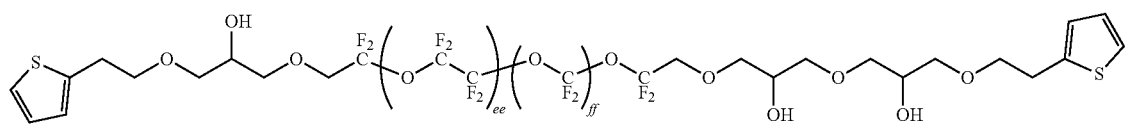
(J)

(In Formula (J), ee and ff each represents 0.1 to 20.)

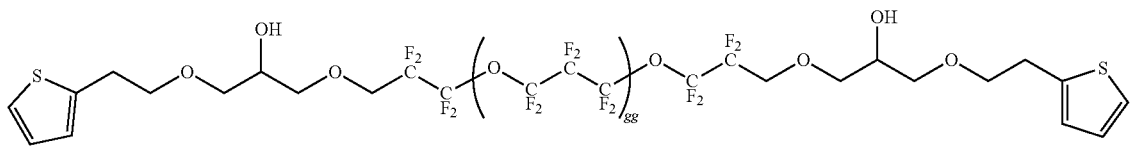

(K)

(In Formula (K), gg represents 0.1 to 20.)

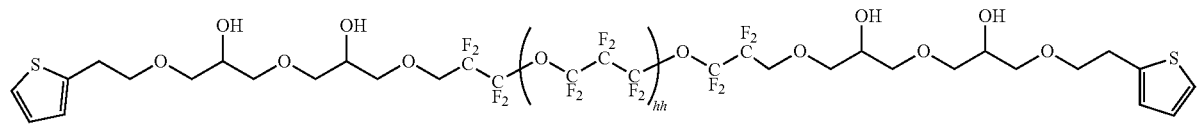

(L)

(In Formula (L), hh represents 0.1 to 20.)

In the fluorine-containing ether compound represented by Formula (1), a number-average molecular weight (Mn) is preferably within a range of 500 to 10000, more preferably within a range of 750 to 7500, and particularly preferably 1000 to 5000.

When the number-average molecular weight is 500 or more, the lubricating layer including the fluorine-containing ether compound of the present embodiment achieves excellent heat resistance. The number-average molecular weight of the fluorine-containing ether compound is more preferably 1000 or more. In addition, when the number-average molecular weight is 10000 or less, the viscosity of the fluorine-containing ether compound is appropriate, and when applying a lubricant including the compound, a lubricating layer having a reduced thickness can be easily formed. The number-average molecular weight of the fluorine-containing ether compound is preferably 5000 or less, from the viewpoint that a viscosity capable of easy handling is obtained in a case of being applied to a lubricant.

The number-average molecular weight (Mn) of the fluorine-containing ether compound is a value measured by $^1$H-NMR and $^{19}$F-NMR using MANCE III 400 manufactured by Bruker Biospin. Specifically, the number of repetition units of the PFPE chain was calculated from an integral value measured by $^{19}$F-NMR, and the number-average molecular weight was determined. In the measurement of NMR (nuclear magnetic resonance), a sample was diluted in hexafluorobenzene/d-acetone (¼v/v) solvent to be used for the measurement. For the standard of $^{19}$F-NMR chemical shift, a peak of the hexafluorobenzene was set to −164.7 ppm. For the standard of $^1$H-NMR chemical shift, a peak of the acetone was set to 2.2 ppm.

A molecular weight dispersity (ratio shown by weight-average molecular weight (Mw)/number-average molecular weight (Mn)) is preferably set to 1.3 or less, by performing molecular-weight fractionation on the fluorine-containing ether compound represented by Formula (1).

There is no need to set particular limitation, but as the molecular-weight fractionation method, for example, molecular-weight fractionation by a silica gel column chromatography method, a gel permeation chromatography (GPC) method, or the like and molecular-weight fractionation by a supercritical extraction method can be used.

"Product Method"

A production method of the fluorine-containing ether compound of the present embodiment is not particularly limited, and a known production method can be used for the production. The fluorine-containing ether compound of the present embodiment can be produced, for example, using the following production method.

For example, a method in which a compound including an epoxy group and a heterocyclic group is reacted in two equivalent amounts with a perfluoropolyether compound having a perfluoropolyether main chain in a molecule and having a hydroxy group at each of both ends of the molecule may be used. Examples of the compound having the epoxy group and the heterocyclic group include compounds represented by Formulas (10) to (15).

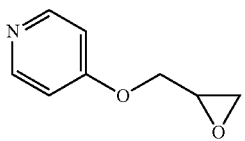

(14)

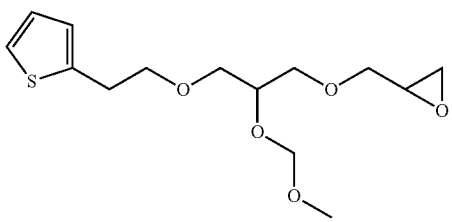

(15)

In the fluorine-containing ether compound of the present embodiment, the group having a heterocyclic ring represented by $R^1$ or $R^5$ is bonded to each of both ends of the PFPE chain represented by $R^3$, via the divalent linking group having a polar group represented by $R^2$ or $R^4$, as shown in Formula (1).

In the lubricating layer including the fluorine-containing ether compound of the present embodiment, the PFPE chain covers the surface of the protective layer and reduces a frictional force between the magnetic head and the protective layer. Furthermore, combination of $R^2$ and $R^4$ with $R^1$ and $R^5$ disposed at both ends of the PFPE chain improves the affinity between the lubricating layer including the fluorine-containing ether compound of the present embodiment and the protective layer. As a result, in a case where a lubricating layer is formed on the protective layer of the magnetic recording medium using the lubricant for a magnetic recording medium (hereinafter, abbreviated as "lubricant" in some cases) including the fluorine-containing ether compound of the present embodiment, even when the thickness is reduced, high coverage is obtained, and it is possible to form a lubricating layer having excellent chemical resistance and wear resistance.

[Lubricant for Magnetic Recording Medium]

The lubricant for a magnetic recording medium of the present embodiment includes the fluorine-containing ether compound represented by Formula (1).

The lubricant of the present embodiment can be used by being mixed with a known material used as a lubricant material as needed, within a range not impairing the characteristics obtained by including the fluorine-containing ether compound represented by Formula (1).

Specific examples of a known material include FOMBLIN (registered trademark) ZDIAC, FOMBLIN ZDEAL, and FOMBLIN AM-2001 (all manufactured by Solvey Solexis), and Moresco A20H (manufactured by Moresco). It is preferable that the known material used by being mixed with the lubricant of the present embodiment has a number-average molecular weight of 1000 to 10000.

In a case where the lubricant of the present embodiment includes other materials in addition to the fluorine-containing ether compound represented by Formula (1), the content of the fluorine-containing ether compound represented by Formula (1) in the lubricant of the present embodiment is preferably 50% by mass or more, more preferably 60% by mass or more, and still more preferably 70% by mass or more, relative to a total amount of the lubricant. The content may preferably be 80% by mass or more, or 90% by mass.

Since the lubricant of be present embodiment includes the fluorine-containing ether compound represented by Formula (1), even if the thickness is reduced, the surface of the protective layer can be covered with high coverage, and it s possible to form a lubricating layer with excellent chemical resistance and wear resistance.

[Magnetic Recording Medium]

The magnetic recording medium of the present embodiment is obtained by providing at least a magnetic layer, a protective layer, and a lubricating layer sequentially on a substrate.

In the magnetic recording medium of the present embodiment, one or more base layers can be provided between the substrate and the magnetic layer, as needed. In addition, an adhesion layer and/or a soft magnetic layer can be provided between the base layer and the substrate.

FIG. 1 is a schematic sectional view showing the magnetic recording medium according to an embodiment of the present invention.

A magnetic recording medium 10 of the present embodiment has a structure in which an adhesion layer 12, a soft magnetic layer 13, a first base layer 14, a second base layer 15, a magnetic layer 16, a protective layer 17, and a lubricating layer 18 are sequentially provided on a substrate 11.

"Substrate"

A nonmagnetic substrate or the like in which a film made of NiP or an NiP alloy is formed on a base substance made of metal or alloy material such as Al or an Al alloy can be used as the substrate 11.

In addition, as the substrate 11, a nonmagnetic substrate made of a nonmetallic material such as glass, ceramics, silicon, silicon carbide, carbon, or resin may be used, and a nonmagnetic substrate in which a film of NiP or an NiP alloy is formed on a base substance made of the nonmetallic materials may also be used.

The glass substrate has rigidity and excellent smoothness. Therefore, the glass substrate is suitable for high recording density. Examples of the glass substrate include an aluminosilicate glass substrate. In particular, a chemically strengthened aluminosilicate glass substrate is suitable.

The roughness of a main surface of the substrate 11 is preferably ultra-smooth in which Rmax is 6 nm or less and Ra is 0.6 nm or less. Here, the surface roughness Rmax and Ra are based on the definition of JIS B 0601.

"Adhesion Layer"

The adhesion layer 12 prevents corrosion of the substrate 11 from progressing, which occurs in a case where the substrate 11 and the soft magnetic layer 13, which is provided on the adhesion layer 12, are disposed in contact with each other.

A material of the adhesion layer 12 can be appropriately selected from, for example, Cr, a Cr alloy, Ti, a Ti alloy, CrTi, NiAl, and an AlRu alloy. The adhesion layer 12 can be formed, for example, by a sputtering method.

"Soft Magnetic Layer"

The soft magnetic layer 13 preferably has a structure in which a first soft magnetic film, an intermediate layer made of a Ru film, and a second soft magnetic film are sequentially laminated. That is, the soft magnetic layer 13 preferably has a structure in which the intermediate layer made of the Ru film is sandwiched between the two soft magnetic films to couple the soft magnetic films above and below the intermediate layer by anti-ferro coupling (AFC).

Examples of materials of the first soft magnetic film and the second soft magnetic film include a CoZrTa alloy and a CoFe alloy.

It is preferable to add any of Zr, Ta, and Nb to the CoFe alloy used for the first soft magnetic film and the second soft magnetic film. Accordingly, amorphization of the first soft magnetic film and the second soft magnetic film is promoted. An orientation of the first base layer (seed layer) can be improved, and flying height of a magnetic head can be reduced.

The soft magnetic layer 13 can be formed, for example, by a sputtering method.

"First Base Layer"

The first base layer 14 is a layer for controlling the orientation and a crystal size of the second base layer 15 and the magnetic layer 16 provided thereon.

Examples of the first base layer 14 include a Cr layer, a Ta layer, a Ru layer, or a layer of a CrMo alloy, a CoW alloy, a CrW alloy, a CrV alloy, or a CrTi alloy.

The first base layer 14 can be formed, for example, by a sputtering method.

"Second Base Layer"

The second base layer 15 is a layer that controls the orientation of the magnetic layer 16 to be favorable. The second base layer 15 is preferably a layer made of Ru or a Ru alloy.

The second base layer 15 may be a layer formed by a single layer or may be formed of a plurality of layers. In a case where the second base layer 15 is formed of a plurality of layers, all the layers may be formed of the same material, or at least one layer may be formed of a different material.

The second base layer 15 can be formed, for example, by a sputtering method.

"Magnetic Layer"

The magnetic layer 16 is formed of a magnetic film in which an easy axis of magnetization is oriented in a direction perpendicular or horizontal to a substrate surface. The magnetic layer 16 is preferably a layer including Co and Pt, and in order to further improve an SNR characteristic, it may be a layer including at least one selected from oxides, Cr, B, Cu, Ta, and Zr.

Examples of the oxide included in the magnetic layer 16 include $SiO_2$, SiO, $Cr_2O_3$, CoO, $Ta_2O_3$, and $TiO_2$.

The magnetic layer 16 may be a layer formed by a single layer or may be formed of a plurality of magnetic layers including a material having a different composition.

For example, in a case where the magnetic layer 16 is formed of three layers of a first magnetic layer, a second magnetic layer, and a third magnetic layer, the first magnetic layer preferably has a granular structure that includes Co, Cr, and Pt, and further includes an oxide. As the oxide included in the first magnetic layer, for example, oxides of Cr, Si, Ta, Al, Ti, Mg, Co, and the like are preferably used. Among these, in particular, $TiO_2$, $Cr_2O_3$, $SiO_2$, and the like can be suitably used. In addition, it is preferable that the first magnetic layer includes a complex oxide obtained by adding two or more kinds of oxides. Among these, in particular, $Cr_2O_3$—$SiO_2$, $Cr_2O_3$—$TiO_2$, and $SiO_2$—$TiO_2$ can be suitably used.

The first magnetic layer can include at least one element selected from B, Ta, Mo, Cu, Nd, W, Nb, Sm, Tb, Ru, and Re, in addition to Co, Cr, Pt, and the oxide.

For the second magnetic layer, the same material as the first magnetic layer can be used. The second magnetic layer preferably has a granular structure.

The third magnetic layer preferably has a non-granular structure including a material that includes Co, Cr, and Pt and does not include an oxide. The third magnetic layer can include at least one element selected from B, Ta, Mo, Cu, Nd, W, Nb, Sm, Tb, Ru, Re, and Mn, in addition to Co, Cr, and Pt.

In a case where the magnetic layer 16 is formed of a plurality of magnetic layers, it is preferable to provide a nonmagnetic layer between adjacent magnetic layers. In a case where the magnetic layer 16 is formed of three layers of the first magnetic layer, the second magnetic layer, and the third magnetic layer, a nonmagnetic layer is preferably provided between the first magnetic layer and the second magnetic layer and between the second magnetic layer and the third magnetic layer.

For the nonmagnetic layer provided between the adjacent magnetic layers of the magnetic layer 16, for example, Ru, a Ru alloy, a CoCr alloy, and CoCrX1 alloy (X1 represents at least one or more elements selected from Pt, Ta, Zr, Re, Ru, Cu, Nb, Ni, Mn, Ge, Si, O, N, W, Mo, Ti, V, Zr, and B) can be suitably used.

For the nonmagnetic layer provided between the adjacent magnetic layers of the magnetic layer 16, it is preferable to use an alloy material including an oxide, a metal nitride, or a metal carbide. Specifically, as the oxide, for example, $SiO_2$, $Al_2O_3$, $Ta_2O_5$, $Cr_2O_3$, MgO, $Y_2O_3$, and $TiO_2$ can be used. As the metal nitride, for example, AlN, $Si_3N_4$, TaN, and CrN can be used. As the metal carbide, for example, TaC, BC, and SiC can be used.

The nonmagnetic layer can be formed, for example, by a sputtering method.

In order to realize higher recording density, the magnetic layer 16 is preferably a magnetic layer for perpendicular magnetic recording in which the easy axis of magnetization is perpendicular the substrate surface, but may be an in-plane magnetic recording.

The magnetic layer 16 may be formed by a vapor deposition method, an ion beam puttering method, a magnetron sputtering method, and any known method of the related art, and is usually formed by the sputtering method.

"Protective Layer"

The protective layer 17 is a layer for protecting the magnetic layer 16. The protective layer 17 may be a layer formed by a single layer or may be formed of a plurality of layers. As the protective layer 17, a carbon-based protective layer can be preferably used, and in particular, an amorphous carbon protective layer is preferable. It is preferable that the protective layer 17 be the carbon-based protective layer, from the viewpoint that the interaction with the polar group (particularly, a hydroxyl group) included in the fluorine-containing ether compound in the lubricating layer 18 is further enhanced.

The adhesion force between the carbon-based protective layer and the lubricating layer 18 can be controlled using the carbon-based protective layer which includes hydrogenated carbon and/or nitrogenated carbon and adjusting the hydrogen content and/or nitrogen content in the carbon-based protective layer. The hydrogen content in the carbon-based protective layer is preferably 3 to 20 atom % as measured by hydrogen forward scattering (HFS). In addition, the nitrogen content in the carbon-based protective layer is preferably 4 to 12 atom % as measured by X-ray photoelectron spectroscopy (XPS).

Hydrogen and/or nitrogen included in the carbon-based protective layer need not be uniformly contained throughout the carbon-based protective layer. For example, it is preferable that the carbon-based protective layer is, for example, a composition gradient layer in which nitrogen is contained on the lubricating layer 18 side of the protective layer 17 and hydrogen is contained on the magnetic layer 16 side of the protective layer 17. In this case, the adhesion force between the magnetic layer 16 and the carbon-based protective layer and between the lubricating layer 18 and the carbon-based protective layer is further enhanced.

A film thickness of the protect layer 17 is preferably 10 to 70 Å. When the film thickness of the protective layer 17 is 10 Å or more, the performance of the protective layer 17 is sufficiently obtained. It is preferable that the film thickness of the protective layer 17 be 70 Å or less from the viewpoint of thinning the protective layer 17.

As the film forming method of the protective layer 17, a sputtering method using a target material containing carbon, a chemical vapor deposition (CVD) method using a hydrocarbon raw material such ethylene or toluene, an ion beam deposition (IBD) method, or the like can be used.

In a ease of forming the carbon-based protective layer as the protective layer 17, a film can be formed, for example, by a DC magnetron sputtering method. In particular, in a case of forming the carbon-based protective layer as the protective layer 17, it is preferable to form an amorphous carbon protective layer by a plasma CVD method. The amorphous carbon protective layer formed by the plasma CVD method has a uniform surface and small roughness.

"Lubricating Layer"

The lubricating layer 18 prevents the magnetic recording medium 10 from being contaminated. In addition, the lubricating layer 18 reduces a frictional force of a magnetic head of a magnetic recording and reproducing apparatus sliding on the magnetic recording medium 10, and improves durability of the magnetic recording medium 10.

As shown in FIG. 1, the lubricating layer 18 is formed on and in contact with the protective layer 17. The lubricating layer 18 is formed by applying the lubricant for a magnetic record medium described above onto the protective layer 17. Therefore, the lubricating layer 18 includes the above fluorine-containing ether compound.

In a case where the protective layer 17 disposed under the lubricating layer 18 is the carbon-based protective layer, in particular, the lubricating layer 18 is bonded to the fluorine-containing ether compound included in the protective layer 17 with high bonding strength. As a result, even when the thickness of the lubricating layer 18 is reduced, the magnetic recording medium 10 in which the surface of the protective layer 17 is covered with high coverage is easily obtained, and it is possible to effectively prevent the surface of the magnetic recording medium 10 from being contaminated.

A predetermined average film thickness of the lubricating layer 18 can be selected, but the average film thickness is preferably, for example, 0.5 nm (5 Å) to 2 nm (20 Å). When the average film thickness of the lubricating layer 18 is 0.5 nm or more, the lubricating layer 18 is formed in a uniform film thickness without being in an island form or a mesh form. Therefore, the surface of the protective layer 17 can be covered with high coverage by the lubricating layer 18. In addition, when setting the average film thickness of the lubricating layer 18 to 2 nm or less, the lubricating layer 18 can be sufficiently thinned, and the flying height of the magnetic head can be sufficiently reduced.

"Forming Method of Lubricating Layer"

In order to form the lubricating layer 18, for example, a method in which a magnetic recording medium in the middle of production, at which each layer up to the protective layer 17 is formed on the substrate 11, is prepared, and the lubricating layer-forming solution is applied onto the protective layer 17, can be used.

The lubricating layer-forming solution is obtained by dispersing and dissolving the lubricant for a magnetic recording medium of the embodiment in a solvent as needed to set a viscosity and concentration suitable for a coating method.

Examples of the solvent used for the lubricating layer-forming solution include a fluorinated solvent such as Vertrel (registered trademark) XF (trade name, manufactured by Du Pont-Mitsui Fluorochemicals Co., Ltd.).

The coating method of the lubricating layer-forming solution is not specifically limited, and examples thereof include a spin coat method, a spray method, a paper coat method, and a dip method.

In a case of using the dip method, for example, the following method can be used. First, the substrate 11 in which each layer up to the protective layer 17 is formed is immersed in the lubricating layer-forming solution contained in an immersion tank of a dip-coating apparatus. Then, the substrate 11 is taken out of the immersion tank at a predetermined speed.

In this way, the lubricating layer-forming solution is applied to the surface on the protective layer 17 of the substrate 11.

By using the dip method, the lubricating layer-forming solution can be uniformly applied to the surface of the protective layer 17, and the lubricating layer 18 can be formed on the protective layer 17 with uniform film thickness.

In the present embodiment, it is preferable to carry out a heat treatment on the substrate 11 in the lubricating layer 18 is formed. By applying the heat treatment, the adhesion between the lubricating layer 18 and the protective layer 17 improves, and the adhesion force between the lubricating layer 18 and the protective layer 17 improves. A predetermined heat-treatment temperature can be selected, but the heat-treatment temperature is preferably, for example, 100° C. to 180° C. When the heat-treatment temperature is 100° C. or higher, an effect of improving the adhesion between the lubricating layer 18 and the protective layer 17 is sufficiently obtained. In addition, when the heat-treatment temperature is set to be 180° C. or lower, it is possible to prevent the lubricating layer 18 from being thermally decomposed. Heat-treatment time is preferably 10 to 120 minutes.

In the present embodiment, in order to further enhance the adhesion force of the lubricating layer 18 to the protective layer 17, irradiation treatment with ultraviolet light (UV) on the lubricating layer 18 of the substrate 11 before or after the heat treatment may also be performed.

The magnetic recording medium 10 of the present embodiment is obtained by providing at least the magnetic layer 16, the protective layer 17, and the lubricating layer 18 sequentially on the substrate 11. In the magnetic recording medium 10 of the present embodiment, the lubricating layer 18 including the fluorine-containing ether compound described above is formed on and in contact with the protective layer 17. The lubricating layer 18 has excellent chemical resistance and wear resistance even when the thickness is reduced. Accordingly, the magnetic recording medium 10 of the present embodiment has excellent reliability, in particular, suppression of silicon contamination and wear resistance. Therefore, the magnetic recording medium 10 of the present embodiment has a low flying height (for example, 10 nm or less) of the magnetic head, and has high reliability that operation can be performed stably over a long period even under severe environments associated with diversification of applications. Therefore, the magnetic recording medium 10 of the present embodiment is particularly suitable as a magnetic disk mounted on an LUL type magnetic disk unit.

EXAMPLES

Hereinafter, the present invention will be further specifically described, using Examples and Comparative Examples. The present invention is not limited to only the following Examples.

Example 1

According to the method shown below, a compound represented by Formula (A) (in Formula (A), q represents 4.5 and r represents 4.5) was obtained.

First, a compound represented by Formula (10) was synthesized using thiophene ethanol and epichlorohydrin.

Fluoropolyether (40.0 g) (number-average molecular weight of 1000 and molecular weight distribution of 1.1) represented by $HOCH_2CF_2O(CF_2CF_2O)_q(CF_2O)_rCF_2CH_2OH$ (in the formula, q represents 4.5 and r represents 4.5) and 15.5 g of a compound represented by Formula (10), and tertiary butyl alcohol (t-BuOH) (20.0 mL) were put into a 200-mL eggplant flask under nitrogen gas atmosphere, and stirred at room temperature to be homogeneous. Further, potassium tertiary butoxide (t-BuOK) (3.6 g) was added to the eggplant flask, heated to 70° C., and stirred for 8 hours to allow the reaction to proceed.

Thereafter, the obtained reaction product was cooled to 25° C. and water was added. Further, an organic layer was extracted by adding Vertrel XF (manufactured by Du Pont-Mitsui Fluorochemicals Co., Ltd.) (hereinafter, Vertrel XF), and washing was performed with water. An organic layer was dehydrated by adding anhydrous sodium sulfate and the desiccant was filtered off. Thereafter, a filtrate was concentrated.

A residue was purified by silica gel column chromatography to obtain the compound (A) (9.0 g).

$^1$H-NMR and $^{19}$F-NMR measurements of the obtained compound (A) were conducted, and a structure was identified from the following results.

$^1$H-NMR (acetone-D6)

3.10 to 3.15 (4H), 3.50 to 3.60 (4H), 3.65 to 3.70 (4H), 3.75 to 3.90 (6H), 4.00 to 4.10 (4H), 6.80 to 6.85 (4H), 7.05 to 7.10 (2H)

$^{19}$F-NMR (acetone-D6)

−59.17 to −56.65 (9F), −79.96 (2F), −81.98 (2F), −90.20 to −91.87 (18F)

Example 2

According to the method shown below, a compound represented by Formula (B) (in Formula (B), k represents 4.5 and m represents 4.5) was obtained.

First, a compound represented by Formula (11) was synthesized using N-methylpyrazole methanol and epichlorohydrin.

Then, a compound (B) was obtained in the same manner as in Example 1, except that 14.1 g of the compound represented by Formula (11) was used instead of the compound represented by Formula (10) used in Example 1.

$^1$H-NMR measurement of the obtained compound (B) was conducted, and a structure was identified from the following results.

$^1$H-NMR (acetone-D6) 3.65 to 3.85 (16H), 4.00 to 4.05 (4H), 4.55 to 4.60 (4H), 6.60 (2H), 7.30 (2H)

Example 3

According to the method shown below, a compound represented by Formula (C) (in Formula (C), n represents 4.5 and p represents 4.5) was obtained.

First, a compound represented by Formula (12) was synthesized using methylthiazole ethanol and epichlorohydrin.

Then, a compound (C) was obtained in the same manner as in Example 1, except that 16.7 g of the compound represented by Formula (12) was used instead of the compound represented by Formula (10) used in Example 1.

$^1$H-NMR measurement of the obtained compound (C) was conducted, and a structure was identified from the following results.

$^1$H-NMR (acetone-D6)

2.35 to 2.40 (6H), 3.00 to 3.10 (4H), 3.65 to 3.85 (10H), 3.90 to 4.00 (4H), 4.55 to 4.60 (4H), 8.45 (2H)

Example 4

According to the method shown below, a compound represented by Formula (D) (in Formula (D), s represents 4.5 and t represents 4.5) was obtained.

First, a compound represented by Formula (13) was synthesized by oxidizing a reaction product of N-methylpyrazole methanol and allyl glycidyl ether.

Then, a compound (D) was obtained in the same manner as in Example 1, except that 20.4 g of the compound represented by Formula (13) was used instead of the compound represented by Formula (10) used in Example 1.

$^1$H-NMR measurement of the obtained compound (D) was conducted, and a structure was identified from the following results.

$^1$H-NMR (acetone-D6)

3.70 to 3.95 (20H), 4.00 to 4.05 (10H), 4.55 to 4.60 (4H), 6.97 (2H), 7.30 (2H)

Example 5

According to the method shown below, a compound represented by Formula (E) (in Formula (E), u represents 4.5 and v represents 4.5) was obtained.

A compound in which a pyrazole compound was bonded to one end of the perfluoropolyether was obtained in the same manner as in Example 2, except that 7.0 g of the compound represented by Formula (11) and 1.8 g of potassium tertiary butoxide (t-BuOK) were used.

3.8 g of the compound represented by Compound (10) and tertiary butyl alcohol (t-BuOH) (20.0 mL) were added to the compound (23.0 g) in which a pyrazole compound was bonded to one end of the perfluoropolyether and stirred at room temperature to be homogeneous. Further, potassium tertiary butoxide (t-BuOK) (0.9 g) was added to the solution that was stirred to be homogeneous, and the mixture was heated to 70° C., and stirred for 8 hours to allow the reaction to proceed.

Water and Vertrel XF were added to the reaction product cooled to 25° C., and an aqueous layer was separated therefrom. An organic layer was dehydrated by adding anhydrous sodium sulfate and the desiccant was filtered off. Thereafter, a filtrate was concentrated. A residue was purified by silica gel column chromatography to obtain a compound (E).

$^1$H-NMR measurement of the obtained compound (E) was conducted, and a structure was identified from the following results.

$^1$H-NMR (acetone-D6)

2.95 to 3.05 (2H), 3.50 to 3.60 (2H), 3.70 to 3.90 (11H), 4.05 to 4.10 (4H), 4.55 to 4.60 (4H), 6.95 to 7.00 (2H), 7.05 (1H), 7.15 to 7.20 (1H), 7.30 (1H)

Example 6

According to the method shown below, a compound represented by Formula (F) (in Formula (F), w represents 4.5 and x represents 4.5) was obtained.

First, a compound represented by Formula (14) was synthesized using hydroxy pyridine and epichlorohydrin.

Then, a compound (F) was obtained in the same manner as in Example 1, except that 12.7 g of the compound represented by Formula (14) was used instead of the compound represented by Formula (10) used in Example 1.

$^1$-NMR measurement of the obtained compound (F) was conducted, and a structure was identified from the following results.

$^1$H-NMR (acetone-D6)

3.65 to 3.85 (6H), 4.00 to 4.05 (4H), 4.55 to 4.60 (4H), 6.60 (4H), 7.88 (4H)

Example 7

According to the method shown below, a compound represented by Formula (I) (in Formula (I), cc represents 4.5 and dd represents 4.5) was obtained.

First, a compound represented by Formula (15) was synthesized according to the method shown below. The compound represented by Formula (10) was hydrolyzed, and a primary hydroxy group of the obtained compound was protected with a t-butyldimethylsilyl group. Thereafter, a secondary hydroxy group was protected with a methoxymethyl group, and the t-butyldimethylsilyl group was removed from the obtained compound. The formed primary hydroxy group was reacted with epibromohydrin to perform synthesis.

Fluoropolyether (40.0 g) (number-average molecular weight of 1000 and molecular weight distribution of 1.1) represented by $HOCH_2CF_2O(CF_2CF_2O)_{cc}(CF_2O)_{dd}CF_2CH_2OH$ (in the formula, cc represents 4.5 and dd represents 4.5) and 25.4 g of a compound represented by Formula (15), and tertiary butyl alcohol (t-BuOH) (20.0 mL) were put into a 200-mL eggplant flask under nitrogen gas atmosphere, and stirred at room temperature to be homogeneous. Further, potassium tertiary butoxide (t-BuOK) (3.6 g) was added to the eggplant flask, heated to 70° C., and stirred for 8 hours to allow the reaction to proceed.

The reaction solution was returned to room temperature, transferred to a separatory funnel containing 50 mL of water, and extracted twice with 100 mL of ethyl acetate, and the organic layer was concentrated. 60 g of a 10% hydrogen chloride/methanol solution was added thereto and stirred at room temperature for 1 hour.

Thereafter, water was added to the obtained reaction product. Further, an organic layer was extracted by adding Vertrel XF (manufactured by DU Pont-Mitsui Fluorochemicals Co., Ltd.) (hereinafter, Vertrel XF), and washing was performed with water. An organic layer was dehydrated by adding anhydrous sodium sulfate and the desiccant was filtered off. Thereafter, a filtrate was concentrated. A residue was purified by silica gel column chromatography to obtain the compound (I) (18.0 g).

$^1$H-NMR measurement of the obtained compound (I) was conducted, and a structure was identified from the following results.

$^1$H-NMR (acetone-D6)

3.05 to 3.10 (4H), 3.48 to 3.56 (12H), 3.67 to 3.69 (6H), 3.70 to 3.90 (6H), 4.07 to 4.12 (4H), 6.90 to 6.94 (4H), 7.23 to 7.25 (2H)

Example 8

According to the method shown below, a compound represented by Formula (J) (in Formula (J), ee represents 4.5 and ff represents 4.5) was obtained.

A compound in which a thiophene compound was bonded to one end of the perfluoropolyether was obtained in the same manner as in Example 1, except that 7.7 g of the compound represented by Formula (10) and 1.8 g of potassium tertiary butoxide (t-BuOK) were used.

6.4 g of the compound represented by Compound (15) and tertiary butyl alcohol (t-BuOH) (20.0 mL) were added to the compound (24.0 g) in which a thiophene compound was bonded to one end of the perfluoropolyether and stirred at room temperature to be homogeneous. Further, potassium tertiary butoxide (t-BuOK) (0.9 g) was added to the solution and stirred to be homogeneous, heated to 70° C., and stirred for 8 hours to allow the reaction to proceed.

The reaction solution was returned room temperature, transferred to a separatory funnel containing 50 mL of water, and extracted twice with 100 mL of ethyl acetate, and the organic layer was concentrated. 60 g of a 10% hydrogen chloride/methanol solution was added thereto and stirred at room temperature for 1 hour.

Thereafter, water was added to the obtained reaction product. Further, an organic layer was extraced by adding Vertrel XF (manufactured by Du Pont-Mitsui Fluorochemicals Co., Ltd.) (hereinafter, Vertrel XF), and washing was performed with water. An organic layer was dehydrated by adding anhydrous sodium sulfate and the desiccant was filtered off. Thereafter, a filtrate was concentrated. A residue was purified by silica gel column chromatography to obtain the compound (J) (14.0 g).

$^1$H-NMR measurement of the obtained compound (J) was conducted, and a structure was identified from the following results.

$^1$H-NMR (acetone-D6)

3.05 to 3.10 (4H), 3.48 to 3.56 (8H), 3.67 to 3.69 (5H), 3.70 to 3.90 (6H), 4.07 to 4.12 (4H), 6.90 to 6.94 (4H), 7.23 to 7.25 (2H)

Example 9

According to the method shown below, a compound represented by Formula (K) (in Formula (K), gg represents 4.5) was obtained.

A compound (K) was obtained in the same manner as in Example 1, except that 40 g of a compound (number-average molecular weight of 1000 and molecular weight distribution of 1.1) represented by $HOCH_2CF_2CF_2O(CF_2CF_2CF_2O)_{gg}CF_2CF_2CH_2OH$ (in the formula, gg represents 4.5) was used instead of the compound (number-average molecular weight of 1000 and molecular weight distribution of 1.1) represented by $HOCH_2CF_2O(CF_2CF_2O)_q(CF_2O)_rCF_2CH_2OH$ (in the formula, q represents 4,5 and r represents 4.5) used in Example 1.

$^1$H-NMR and $^{19}$F-NMR measurements of the obtained compound (K) were conducted, and a structure was identified from the following results.

$^1$H-NMR (acetone-D6)

3.10 to 3.15 (4H), 3.50 to 3.60 (4H), 3.65 to 3.70 (4H), 3.75 to 3.90 (6H), 4.30 to 4.40 (4H), 6.80 to 6.85 (4H). 7.05 to 7.10 (2H)

$^{19}$F-NMR (acetone-D6)

−83.70 (18F), −86.55 (4F), −124.21 (4F), −129.73 (9F)

Example 10

According to the method shown below, a compound represented by Formula (L) (in Formula (L), hh represents 4.5) was obtained.

A compound (L) was obtained in the same manner as in Example 7, except that 40 g of a compound (number-average molecular weight of 1000 and molecular weight distribution of 1.1) represented by $HOCH_2CF_2CF_2O(CF_2CF_2CF_2O)_{hh}CF_2CF_2CH_2OH$ (in the formula, hh represents 4.5) was used instead of the compound (number-average molecular weight of 1000 and molecular weight distribution of 1.1) represented by $HOCH_2CF_2O(CF_2CF2O)_{cc}(CF_2O)_{dd}CF_2CH_2OH$ (in the formula, cc represents 4.5 and dd represents 4.5) used in Example 7.

$^1$H-NMR measurement of the obtained compound (L) was conducted, and a structure was identified from the following results.

$^1$H-NMR (acetone-D6)

3.05 to 3.10 (4H), 3.48 to 3.56 (12H), 3.67 to 3.69 (6H), 3.70 to 3.90 (6H), 4.30 to 4.40 (4H), 6.90 to 6.94 (4H), 7.23 to 7.25 (2H)

Comparative Example 1

A compound represented Formula (G) was synthesized by the method described in Patent document 1.

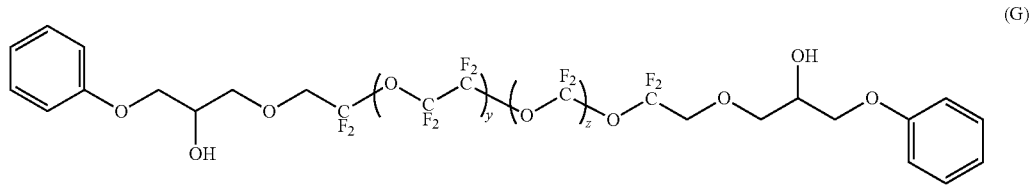

(In Formula (G), y represents 4.5 and z represents 4.5.)

Comparative Example 2

A compound represented by Formula (H) was synthesized by the method described in Patent document 3.

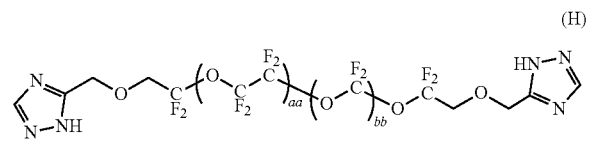

(In Formula (H), aa represents 4.5 and bb represents 4.5.)

The number-average molecular weights of the compounds of Examples 1 to 6 and Comparative Examples 1 and 2 obtained as such were determined by the $^1$H-NMR and $^{19}$F-NMR measurements described above. Results thereof are shown in Table 1.

TABLE 1

| | Compound | Number-average molecular weight | Film thickness (Å) | Sliding time until coefficient of friction sharply increases (sec) | Si adsorption amount |
|---|---|---|---|---|---|
| Example 1 | (A) | 1364 | 9.0 | 940 | 0.68 |
| Example 2 | (B) | 1336 | 9.5 | 955 | 0.65 |
| Example 3 | (C) | 1394 | 9.0 | 930 | 0.70 |
| Example 4 | (D) | 1482 | 10.0 | 925 | 0.64 |
| Example 5 | (E) | 1349 | 9.1 | 935 | 0.66 |
| Example 6 | (F) | 1302 | 9.2 | 922 | 0.69 |
| Example 7 | (I) | 1516 | 9.1 | 969 | 0.61 |
| Example 8 | (J) | 1442 | 9.3 | 952 | 0.65 |
| Example 9 | (K) | 1368 | 9.2 | 911 | 0.70 |
| Example 10 | (L) | 1518 | 9.2 | 924 | 0.64 |
| Comparative Example 1 | (G) | 1296 | 10.5 | 600 | 1.00 |
| Comparative Example 2 | (H) | 1160 | 11.0 | 510 | 0.95 |

Next, according to the method shown below, a lubricating layer-forming solution was prepared using the compounds obtained in Examples 1 to 10 and Comparative Examples 1 and 2. Then, according to the method shown below, the lubricating layer of the magnetic recording medium was formed using the obtained lubricating layer-forming solution, and magnetic recording media of Examples 1 to 10 and Comparative Examples 1 and 2 were obtained.

"Lubricating Layer-Forming Solution"

Each of the compounds obtained in Examples 1 to 10 and Comparative Examples 1 and 2 was dissolved in Vertrel (registered trademark) XF (trade name, manufactured by Du Pont-Mitsui Fluorochemicals Co., Ltd.) as a fluorinated solvent, was diluted with Vertrel, such that the film thickness when applied to the protective layer was 9 Å to 11 Å, to obtain a lubricating layer-forming solution in which a concentration of the compound was 0.0005% by mass to 0.001% by mass.

"Magnetic Recording Medium"

A magnetic recording medium in which an adhesion layer, a soft magnetic layer, a first base layer, a second base layer, a magnetic layer, and a protective layer were sequentially provided on a substrate having a diameter of 65 min was prepared. The protective layer was formed from carbon.

The lubricating layer-forming solutions of Examples 1 to 10 and Comparative Examples 1 and 2 were applied by a dip method onto the protective layer of the magnetic recording medium in which each layer up to the protective layer was formed.

Thereafter, the magnetic recording medium to which the lubricating layer-forming solution was applied was put into a thermostatic chamber at 120° C., and heat treatment was performed for 10 minutes. Accordingly, a lubricating layer was formed on the protective layer to obtain the magnetic recording medium.

A film thickness of lubricating layers of the obtained magnetic recording medium of Examples 1 to 10 and Comparative Examples 1 and 2 was measured using FT-IR (trade name: Nicolet iS50, manufactured by Thermo Fisher Scientific). Results thereof are shown in Table 1.

In addition, a wear resistance test and a chemical resistance test were conducted on the magnetic recording media of Examples 1 to 10 and Comparative Examples 1 and 2, according to the method shown below. Results thereof are shown in Table 1.

(Wear Resistance Test)

Using a pin-on-disk type friction and wear tester, an alumina ball having a diameter of 2 mm as a contact was slid on the lubricating layer of the magnetic recording medium with a load of 40 gf at a sliding speed of 0.25 m/sec to measure a coefficient of friction of a surface of the lubricating layer. Then, sliding time until the coefficient of friction of the surface of the lubricating layer sharply increases was measured. The sliding time until coefficient of friction sharply increases was measured four times for each lubricating layer of the magnetic recording medium, and an average value (time) thereof was used as an indicator of the wear resistance of the lubricant coating film.

The time until the coefficient of friction sharply increases can be used as an indicator of the wear resistance of the lubricating layer for the following reason. In the lubricating layer of the magnetic recording medium, wear progresses according to use of the magnetic recording medium. When the lubricating layer disappears due to wear, the contact and the protective layer are in direct contact with each other, thus causing the coefficient of friction to sharply increase.

As shown in Table 1, the magnetic recording media of Examples 1 to 10 have a longer sliding time, until the coefficient of friction increases sharply, and were more favorable in wear resistance compared to the magnetic recording media of Comparative Examples 1 and 2.

It is presumed that this is because in the magnetic recording media of Examples 1 to 10, in the compound represented by Formula (1) which forms the lubricating layer, $R^1$ and $R^5$ each represents a group having a heterocyclic ring, and $R^2$ and $R^4$ each represents a divalent linking group having a polar group.

(Chemical Resistance Test)

According to the evaluation method shown below, contamination of the magnetic recording medium was investigated using an environmental substance that produces contaminant in a high-temperature environment. In the evaluation method shown below, Si ions were used as be environmental substance, and an Si adsorption amount was measured as the amount of the contaminant formed by the environmental substance and which contaminated the magnetic recording medium.

Specifically, the magnetic recording medium to be evaluated was kept for 240 hours in the presence of siloxane Si rubber under a high-temperature environment at a temperature of 85° C. and a humidity of 0%. Next, the Si adsorption amount on the surface of the magnetic recording medium was analyzed and measured using secondary ion mass spectrometry (SIMS) to evaluate the degree of contamination due to the Si ions as the Si adsorption amount. In the evaluation of the Si adsorption amount, evaluation was performed using a numerical value when the result of Comparative Example 1 was set to 1.00. Results thereof are shown in Table 1.

As shown in Table 1, it is clear that the magnetic recording media of Examples 1 to 10 have a small Si adsorption amount and are less likely to be contaminated by the environmental substance under a high-temperature environment as compared to the magnetic recording media of Comparative Examples 1 and 2.

INDUSTRIAL APPLICABILITY

A fluorine-containing ether compound is provided, which can be suitably used as a material of a lubricant for a magnetic recording medium, and which can form a lubricating layer having excellent chemical resistance and wear resistance, even when the thickness s reduced.

REFERENCE SIGNS LIST

10: Magnetic recording medium
11: Substrate
12: Adhesion layer
13: Soft magnetic layer
14: First base layer
15: Second base layer
16: Magnetic layer
17: Protective layer
18: Lubricating layer

The invention claimed is:

1. A fluorine-containing ether compound represented by Formula (1)

$$R^1\text{—}R^2\text{—}CH_2\text{—}R^3\text{—}CH_2\text{—}R^4\text{—}R^5 \tag{1}$$
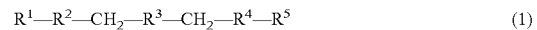

(in Formula (1), $R^1$ and $R^5$ each represents a group having a heterocyclic ring, wherein the heterocyclic ring is at least a pyrazole ring, a thiophene ring, a thiazole ring, or a pyridine ring, $R^1$ and $R^5$ may be the same as or different from each other, $R^2$ and $R^4$ are each represented by Formula (2-1) or (2-2), and $R^3$ represents a perfluoropolyether chain)

$$\text{—(O—CH}_2\text{CH(OH)CH}_2)_a\text{—O—} \tag{2-1}$$

(in Formula (2-1), a represents an integer selected from 1 to 3)

$$\text{—(O—CH}_2\text{CH(CH}_2\text{OH)CH}_2)_b\text{—O—} \tag{2-2}$$
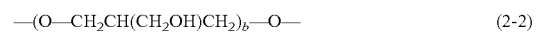

(in Formula (2-2), b represents an integer selected from 1 to 3).

2. The fluorine-containing ether compound according to claim 1, wherein $R^3$ is represented by any of Formulas (3) to (5)

$$\text{—CF}_2\text{—(OCF}_2\text{CF}_2)_c\text{—(OCF}_2)_d\text{—OCF}_2\text{—} \tag{3}$$
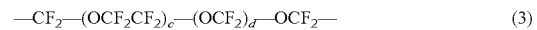

(in Formula (3), c and d each represents 0 to 20, where c or d is 0.1 or more)

$$\text{—CF(CF}_3)\text{—(OCF(CF}_3)\text{CF}_2)_e\text{—OCF(CF}_3)\text{—} \tag{4}$$
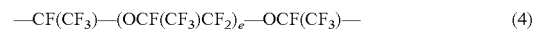

(in Formula (4), e represents 0.1 to 20)

$$\text{—CF}_2\text{CF}_2\text{—(OCF}_2\text{CF}_2\text{CF}_2)_f\text{—OCF}_2\text{CF}_2\text{—} \tag{5}$$

(in Formula (5), f represents 0.1 to 20).

3. The fluorine-containing ether compound according to claim 1, wherein a number-average molecular weight is within a range of 500 to 10000.

4. A lubricant for a magnetic recording medium, comprising:
  the fluorine-containing ether compound according to claim 1.

5. A magnetic recording medium, comprising:
  a substrate; and
  at least a magnetic layer, a protective layer, and a lubricating layer sequentially provided on the substrate,
  wherein the lubricating layer includes the fluorine-containing ether compound according to claim 1.

6. The magnetic recording medium according to claim 5, wherein an average film thickness of the lubricating layer is 0.5 nm to 2 nm.

7. The fluorine-containing ether compound according to claim 1, wherein $R^1$ and $R^5$ in Formula (1) are each represented by one selected from Formulas (6) to (9)

$$Z— \quad (6)$$

(in Formula (6), Z represents a heterocyclic ring which may have a substituent), $$Z—O—(CH_2)_g— \quad (7)$$

(in Formula (7), Z represents a heterocyclic ring which may have a substituent, and g represents an integer selected from 1 to 3)

$$Z—(CH_2)_h— \quad (8)$$

(in Formula (8), Z represents a heterocyclic ring which may have a substituent, and h represents an integer selected from 1 to 3)

$$Z—(CH_2)_i—O—(CH_2)_j— \quad (9)$$

(in Formula (9), Z represents a heterocyclic ring which may have a substituent, and i and j each represents an integer selected from 1 to 3),
  wherein the heterocyclic ring is at least a pyrazole ring, a thiophene ring, a thiazole ring, or a pyridine ring.

8. The fluorine-containing ether compound according to claim 1, which is a compound selected from compounds represented by Formulas (A) to (F) and (I) to (L)

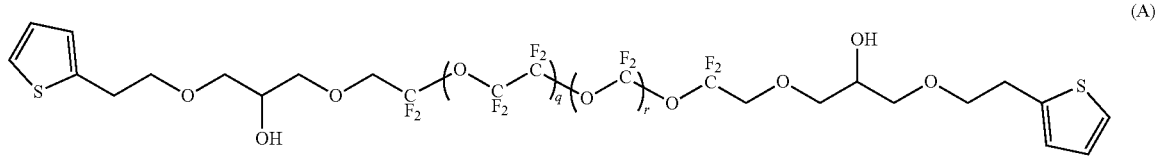

(A)

(in Formula (A), q and r each represents 0.1 to 20)

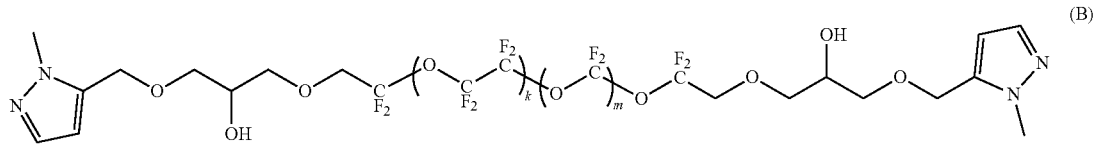

(B)

(in Formula (B), k and m each represents 0.1 to 20)

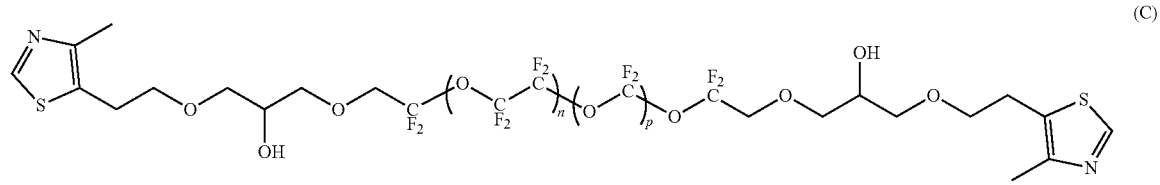

(C)

(in Formula (C), n and p each represents 0.1 to 20)

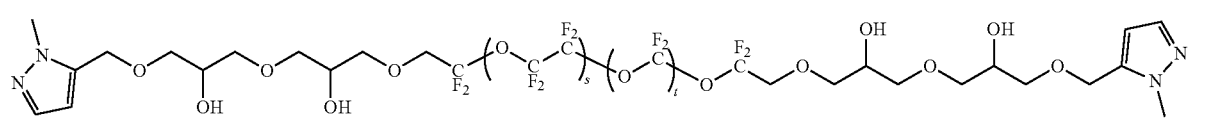

(D)

(in Formula (D), s and t each represents 0.1 to 20)
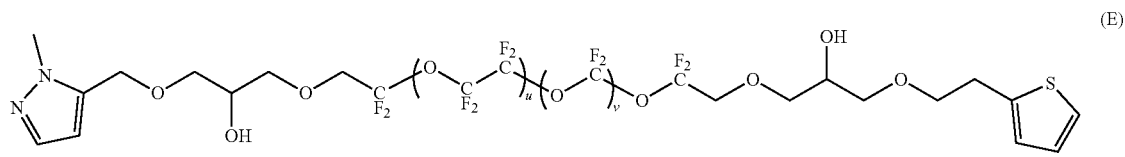
(E)
(in Formula (E), u and v each represents 0.1 to 20)
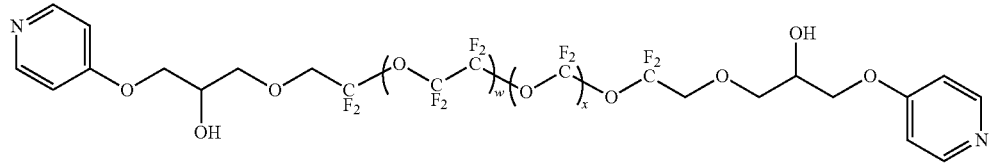
(F)
(in Formula (F), w and x each represents 0.1 to 20)
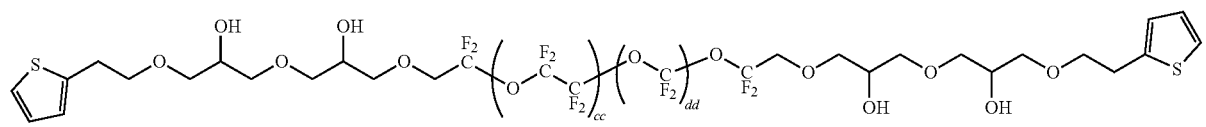
(I)
(in Formula (I), cc and dd each represents 0.1 to 20)
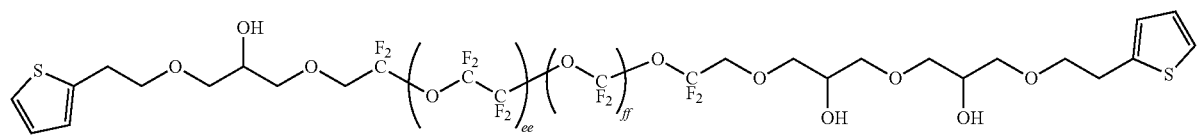
(J)
(in Formula (J), ee and ff each represents 0.1 to 20)
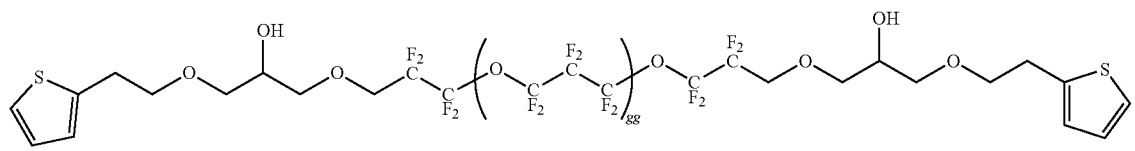
(K)
(in Formula (K), gg represents 0.1 to 20)
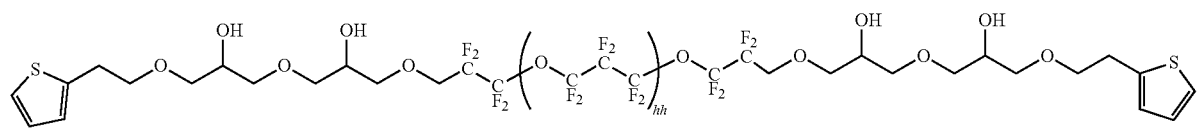
(L)
(in Formula (L), hh represents 0.1 to 20).

9. The fluorine-containing ether compound according to claim 1, wherein $R^2$ and $R^4$ in Formula (1) are each represented by Formula (2-1).

10. The fluorine-containing ether compound according to claim 1, wherein $R^2$ and $R^4$ in Formula (1) are each represented by Formula (2-2).

11. The fluorine-containing ether compound according to claim 1,
wherein $R^3$ is represented by any of Formulas (3) to (5), and $R^1$ and $R^5$ in Formula (1) are each represented by one selected from Formulas (6) to (9)

$$—CF_2—(OCF_2CF_2)_c—(OCF_2)_d—OCF_2— \quad (3)$$

(in Formula (3), c and d each represents 0 to 20, where c or d is 0.1 or more)

$$—CF(CF_3)—(OCF(CF_3)CF_2)_e—OCF(CF_3)— \quad (4)$$

(in Formula (4), e represents 0.1 to 20)

$$—CF_2CF_2—(OCF_2CF_2CF_2)_f—OCF_2CF_2— \quad (5)$$

(in Formula (5), f represents 0.1 to 20)

$$Z— \quad (6)$$

(in Formula (6), Z represents a heterocyclic ring which may have a substituent)

$$Z—O—(CH_2)_g— \quad (7)$$

(in Formula (7), Z represents a heterocyclic ring which may have a substituent, and g represents an integer selected from 1 to 3)

$$Z—(CH_2)_h— \quad (8)$$

(in Formula (8), Z represents a heterocyclic ring which may have a substituent, and h represents an integer selected from 1 to 3)

$$Z—(CH_2)_i—O—(CH_2)_j— \quad (9)$$

(in Formula (9), Z represents a heterocyclic ring which may have a substituent, and i and j each represents an integer selected from 1 to 3),
wherein the heterocyclic ring is at least a pyrazole ring, a thiophene ring, a thiazole ring, or a pyridine ring.

* * * * *